United States Patent [19]

Tsai et al.

[11] Patent Number: 4,785,115
[45] Date of Patent: Nov. 15, 1988

[54] BENZAZOLE SUBSTITUTED TEREPHTHALIC ACID MONOMERS

[75] Inventors: Tsu-Tzu Tsai, Dayton; Fred E. Arnold, Centerville, both of Ohio

[73] Assignee: The United States of America as represented by the Secretary of the United States, Washington, D.C.

[21] Appl. No.: 84,784

[22] Filed: Aug. 13, 1987

[51] Int. Cl.$^4$ .................. C07D 263/56; C07D 277/66
[52] U.S. Cl. .................................... 548/180; 526/257; 526/260; 548/224
[58] Field of Search ........................ 548/180, 224, 236; 526/257, 260; 524/83, 87

[56] References Cited

U.S. PATENT DOCUMENTS

| | | | |
|---|---|---|---|
| 3,293,258 | 12/1966 | Siegrist | 548/224 |
| 3,551,443 | 12/1970 | Duennenberger | 548/224 |
| 3,575,996 | 4/1971 | Liechti | 548/224 |
| 3,661,849 | 5/1972 | Culbertson | 548/224 |
| 3,993,659 | 11/1976 | Meyer | 548/224 |
| 4,659,360 | 4/1987 | Baum | 548/224 |

OTHER PUBLICATIONS

Acheson, R. M. (1968) J. Chem. Soc. (C), pp. 1623–1629.

Young. P. (1973) J. Heterocyclic Chem, 10(3), pp. 325–332.

Tsai, F. (1986) Polymer Preprints (ACS), 27(2), pp. 221–222.

Primary Examiner—Donald G. Daus
Assistant Examiner—Mark W. Noel
Attorney, Agent, or Firm—Donald J. Singer; Charles E. Bricker

[57] ABSTRACT

Provided are benzazole-substituted terephthalic acids of the formula

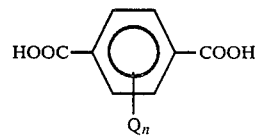

wherein n is 1 or 2 and Q is

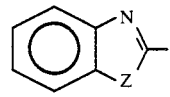

wherein Z is —O— or —S—.

Also provided are methods for preparing the benzazole substituted terephthalic acid compounds.

5 Claims, No Drawings

BENZAZOLE SUBSTITUTED TEREPHTHALIC ACID MONOMERS

RIGHTS OF THE GOVERNMENT

The invention described herein may be manufactured and used by or for the Government of the United States for all governmental purposes without the payment of any royalty.

BACKGROUND OF THE INVENTION

This invention relates to benzazole substituted terephthalic acid compounds.

In general, the class of aromatic heterocyclic extended chain polymers are well known for their outstanding thermal, physical and chemical properties. These polymers generally exhibit excellent modulus and tenacity properties, but lack good properties when in compression, which limits their use as reinforcing structural fibers.

It is an object of the present invention to provide novel benzazole substituted terephthalic acid monomers. These monomers may be used for making aromatic heterocyclic polymers which exhibit improved compressive properties.

Other objects, aspects and advantages of the present invention will be apparent to those skilled in the art from a reading of the following detailed disclosure of the invention.

SUMMARY OF THE INVENTION

In accordance with the present invention there are provided heterocyclic terephthalic acids of the formula

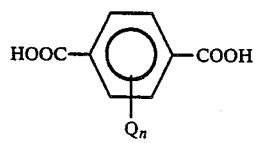

I wherein n is 1 or 2 and Q is

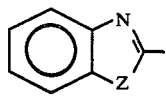

wherein Z is —O— or —S—.

Also provided are methods for preparing the benzazole substituted terephthalic acid compounds.

DESCRIPTION OF THE PREFERRED EMBODIMENTS

The heterocyclic terephthalic acids (I) are prepared according to one of the following reaction schemes:

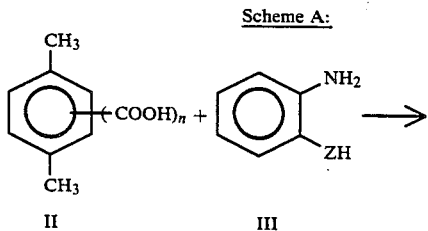

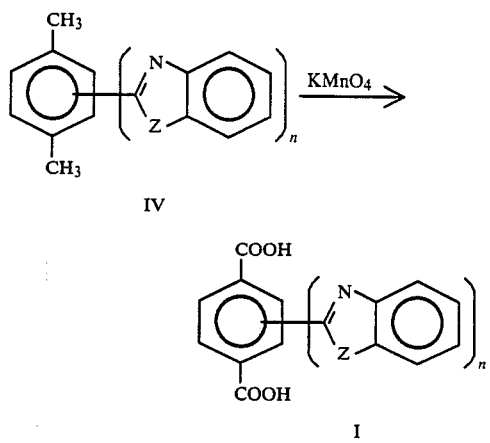

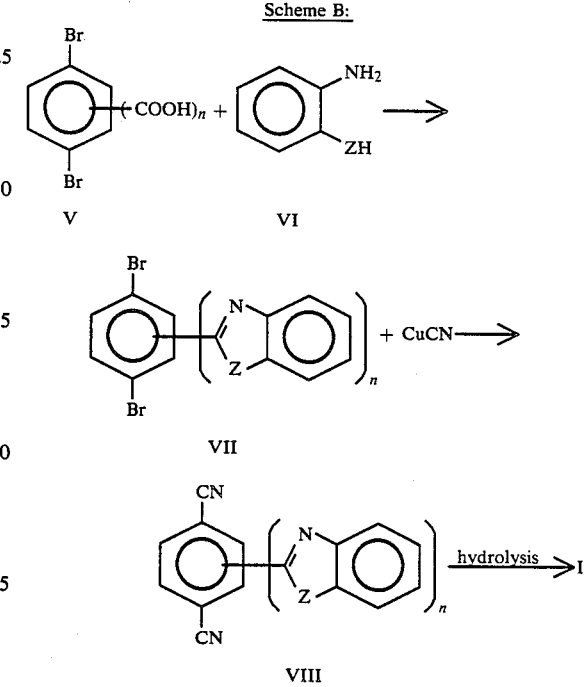

In the reactions given above, Z is —O— or —S— and n is 1 or 2, both previously defined.

As shown by reaction Scheme A, a mono- or di-carboxy-p-xylene is reacted with o-aminophenol or o-aminothiophenol to provide the corresponding pendant heterocyclic p-xylene. The reaction is carried out in polyphosphoric acid under an inert atmosphere at a temperature of about 100 to 200 deg-C. for a period of about 18 to 36 hours. At the end of the reaction period, the mono- or di-heterocyclic p-xylene is precipitated from solution by pouring the reaction mixture into an excess of water. The crude product may, if desired, be purified using techniques known in the art. The pendant heterocyclic p-xylene is oxidized to the corresponding pendant heterocyclic terephthalic acid using any technique known in the art, such as by oxidation of the methyl groups with potassium permanganate in pyridine/aqueous KOH.

As shown by reaction Scheme B, a mono- or di-carboxy-p-dibromobenzene is reacted with o-aminophenol or o-aminothiophenol to provide the corresponding pendant hereocyclic p-dibromobenzene. The reaction is carried out in a solvent mixture of polyphosphoric acid and a suitable liquid carrier for the acid, such as 2,3,4,5-tetrahydrothiophene-1,1-dioxide (sulfolane), at a temperature of about 100 to 200 deg-C for a period of about 18 to 36 hours under an inert atmosphere. At the end of the reaction period, the mono- or di-heterocyclic-p-dibromobenzene is precipitated from solution by pouring the reaction mixture into an excess of water. The crude product may, if desired, be purified using techniques known in the art.

The pendant heterocyclic-p-dibromobenzene is converted to the corresponding dicyano compound using any technique known in the art, such as by treating the former with cuprous cyanide in a suitable solvent, such as N-methyl-2-pyrrolidone, at an elevated temperature, e.g., at reflux, for about 12 to 24 hours. At the end of the reaction period, the dicyano compound is precipitated from solution by pouring the reaction mixture into an aqueous alkali metal cyanide solution. The crude product may be purified using any technique known in the art. Hydrolysis of the dicyano compound may be carried out using any technique known in the art and yields the desired pendant heterocyclic terephthalic acid.

The benzazole substituted terephthalic acids of this invention are useful in preparing polymers having repeating units of the formula:

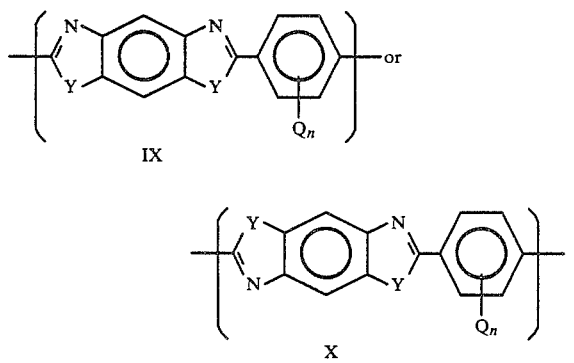

wherein Y is —O—, —S—, or —NH—, n is 1 or 2, and Q is as defined above.

The above polymers are prepared by reacting an amine monomer having the structure

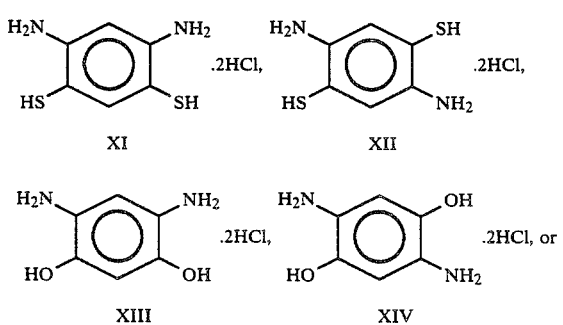

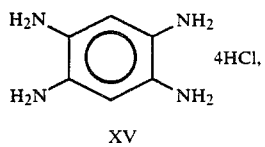

with a benzazole substituted terephthalic acid of this invention.

The polymers IX or X may be prepared by:

a. mixing an amino monomer (XI - XV) with or without oxidation protecting atoms or groups, e.g., HCl groups, with a preliminary solvent of phosphoric acid having a relatively low phosphorous pentoxide content, about 63 to 83%, preferably below about 80%.

b. heating and optionally placing the resulting mixture under reduced pressure to remove any volatile protecting atoms or groups present and provide a mixture of the amino monomer in the preliminary solvent. This step, as well as subsequent steps, is preferably carried out under an inert gas atmosphere. Suitable inert gases include helium, nitrogen, and argon. Heating the mixture to about 70°–90° C. for about 6 to 24 hours is generally sufficient to remove any volatile products.

c. adding the heterocyclic terephthalic acid monomer (I) to the mixture resulting from step b to provide a mixture of amino monomer and acid monomer in the preliminary solvent.

d. increasing the phosphorous pentoxide content of the mixture resulting from step c to provide a reaction medium in which the percentage of phosphorous pentoxide should be about 82 to 86% $P_2O_5$, preferably about 82 to 84% at the end of the polymerization.

e. causing polymerization of the monomers at a temperature of about 100° to 200° C. for about 18 to 36 hours. In a presently preferred embodiment, the reaction temperature is increased gradually during the reaction period, e.g., 170° C. for 20 hours, then 190° C. for 4 hours.

Optionally, steps a, b and c may be combined by by adding the amino and terephthalic acid monomers to the preliminary phorphoric acid solvent, then removing any volatiles, after which the $P_2O_5$ content is raised and the polymerization is carried out.

At the end of the reaction period, the polymer may be precipitated from solution by pouring the reaction mixture into water. The polymer is purified by washing with water until all phosphoric acid is removed. After allowing the polymer to air dry, it is dissolved in methanesulfonic acid, filtered, inversely precipitated with methanol, stirred with concentrated ammmonium hydroxide, and washed with water. The ammonia free water solution is then filtered and washed with methanol and methanol-benzene mixtures, gradually changing to 100 percent benzene. The swollen polymer is frozen and finally dried under reduced pressure to give a purified polymer having a high molecular weight.

The polymer compositions may be formed into fibers of high quality by spinning them into suitable baths such as by wet and "air gap" spinning techniques, using spinnerets and other apparatus constructed of materials resistant to the strong acids used. In "air gap" spinning, the spinneret is usually located in air or in an inert gaseous medium a short distance, e.g., 1 to 24 cm, above the surface of a coagulating bath. Techniques for fiber spinning are well known in the art.

The polymer compositions are optically anisotropic, i.e., microscopic regions of a given extended chain composition are birefringent; a bulk extended chain composition sample depolarizes plane-polarized light because the light transmission properties of the microscopic areas of the extended chain composition vary with direction. This characteristic is associated with the existence of at least part of the extended chain polymer compositions in the liquid crystalline or mesomorphic state.

The extended chain polymer compositions that exhibit optical anisotropy do so while the extended chain polymer compositions are in the relaxed state. This in in contrast to conventional polymer solutions which may be caused to depolarize plane-polarized light when subjected to appreciable shear.

The liquid crystalline extended chain polymer compositions are extremely suitable for spinning into highly ordered and high strength fibers. Such fibers are useful as reinforcement substitutes for other inorganic or organic products.

The above polymers may also be employed in any use typically performed by engineering thermoplastic materials, such a metal replacements and those areas where high performance is necessary.

Intrinsic viscosity is determined by extrapolation of $\eta(rel) -1/c$ and $\ln \eta(rel)/c$ to zero concentration in methane sulfonic acid at 30° C.

The following examples illustrate the invention:

EXAMPLE I

SYNTHESIS OF 2-BENZOXAZOLE p-XYLENE

2-Aminophenol (18.8 g. 0.17 mol), 2,5-dimethylbenzoic acid (27.0 g, 0.18 mol) and 215 g of polyphosphoric acid (PPA) was heated under nitrogen at 145° C. for 24 hours. The reaction mixture, after cooling down to about 50° C., was poured into water to precipitate a heavy oily material. The material was extracted repeatedly with methylene chloride. The methylene chloride solutions were combined, separated, dried over magnesium sulfate, filtered, then evaporated using a rotary evaporator to yield a wet solid. The solid was purified by column chromatography on alumina, eluting with a 3:1 mixture of hexane and methylene chloride. Yield 14.7 g. (39%) m.p. 46°–48° C. Anal. for $C_{15}H_{13}NO$:
Calculated: C, 80.69; H, 5.87; N, 6.27;
Found: C, 80.62; H, 6.02; N, 6.46

EXAMPLE II

SYNTHESIS OF 2-BENZOXAZOLE TEREPHTHALIC ACID

Into a 1 liter three-necked flask was added 10.0 g( 0.045 mol) of 2-benzoxazole-p-xylene, 110 ml of pyridine and 200 ml of 5% NaOH solution. After the reaction mixture was heated to reflux, 100 g of $KMnO_4$ was added, with good stirring. During the addition, the temperature was maintained at 100° C. After the addition, the reaction mixture was heated at reflux overnight. After the reaction mixture cooled to below 100° C., 30 ml of ethanol was added thereto to destroy any excess $KMnO_4$. The mixture was stirred about 30 minutes, then filtered. The solid was washed repeatedly with hot water. The filtrate was acidified with dilute HCl solution to precipitate the expected acid. Yield, 7.5 g (59%). Pure acid having a melting point of 284.5° C. was obtained by recrystallization from glacial acetic acid.

Anal. for $C_{15}H_8NO_5$:
Calculated: C, 63.61; H, 3.20; N, 4.95;
Found: C, 63.38; H, 3.22; N, 5.06.

EXAMPLE III

SYNTHESIS OF 2-BENZOTHIAZOLE-p-XYLENE

2-Aminothiophenol (28.8 g, 0.224 mol), 2,5-dimethylbenzoic acid (33.6 g, 0.224 mol) and 300 g of polyphosphoric acid (PPA) was heated under nitrogen at 140° C. for 24 hours. The reaction mixture, after cooling down to about 50° C., was poured into water to precipitate the compound. The compound was taken up in chlorform and washed with dilute NaOH solution to remove residual acid. The chloroform solution was dried over magnesium sulfate, filtered, then evaporated using a rotary evaporator to yield 52.0 g. (96%) of expected compound.

The crude compound was dissolved in anhydrous ethanol, treated with charcoal and filtered. Water was added to the filtrate until white solid formed permanently. Cooling overnight gave 47.0 g of white crystals, m.p. 58° C.

Anal. for $C_{15}H_{13}SN$:
Calculated: C, 75.25; H, 5.47; N, 5.85; S, 13.40;
Found: C, 74.66; H, 5.54; N, 5.73; S, 13.34.

EXAMPLE IV

SYNTHESIS OF 2-BENZOTHIAZOLE TEREPHTHALIC ACID

Into a 1 liter three-necked flask was added 10.0 g( 0.042 mol) of 2-benzothiazole-p-xylene, 110 ml of pyridine and 200 ml of 5% NaOH solution. After the reaction mixture was heated to reflux, 100 g of $KMnO_4$ was added, with good stirring. During the addition, the temperature was maintained at 100° C. After the addition, the reaction mixture was heated at reflux overnight. After the reaction mixture cooled to below 100° C., 30 ml of ethanol was added thereto to destroy any excess $KMnO_4$. The mixture was stirred about 30 minutes, then filtered. The solid was washed repeatedly with hot water. The filtrate was acidified with dilute HCl solution to precipitate the expected acid. Yield, 5.8 g (46%). Pure acid having a melting point of 287°–8° C. was obtained. by recrystallization from glacial acetic acid.

Anal. for $C_{15}H_9NSO_4$:
Calculated: C, 60.19; H, 3.03; N, 4.08; S, 10.70;
Found: C, 60.13; H, 3.17; N, 4.63; S, 10.71.

EXAMPLE V

SYNTHESIS OF 2,5-BISBENZOTHIAZOLE-p-XYLENE

2-Aminothiophenol (14.2 g, 0.11 mol), 2,5-dicarboxyl-p-xylene (10.1 g, 0.052 mol) and 342 g of 115% polyphosphoric acid (PPA) was heated under nitrogen at 140° C. for 24 hours. The reaction mixture, after cooling down to about 100° C., was poured into water to precipitate the compound. The compound was filtered, washed with dilute NaOH solution and water, then air dried. Yield 16.0 g. (84%) of expected compound. The crude compound was recrystallized from methylene chloride, m.p. 201° C.

Anal. for $C_{22}H_{16}N_2S_2$:
Calculated: C, 70.94; H, 4.33; N, 7.52; S, 17.21;
Found: C, 71.06; H, 4.54; N, 7.01; S, 17.21.

EXAMPLE VI

2,5-BISBENZOTHIAZOLE TEREPHTHALIC ACID

Into a 1 liter three-necked flask was added 4.0 g( 0.01 mol) of 2,5-bisbenzothiazole-p-xylene, 110 ml of pyridine and 200 ml of 5% KOH solution. After the reaction mixture was heated to 95° C., 27 g of KMnO$_4$ was slowly added, with stirring. After the addition, the reaction mixture was heated to reflux for 16 hours. The mixture was filtered and the filtrate was neutralized with dilute HCl solution to precipitate the expected acid. Pure acid having a melting point of 315° C. was obtained by dissolving the acid in NaOH solution, treating the resulting solution with charcoal, filtering and precipitating the acid with HCl. Yield, 0.14 g (3 %).

Anal. for $C_{22}H_{12}N_2S_2O_4$:
Calculated: C, 61.10; H, 2.80; N, 6.48; S, 14.83;
Found: C, 60.26; H, 2.94; N, 6.03; S, 14.72.

EXAMPLE VII

SYNTHESIS OF 2-BENZOXAZOLE-p-DIBROMOBENZENE

A mixture of 2,5-dibromobenzoic acid (31.2 g, 0.10 mol), 2-amino phenol (10.9 g, 0.10 mol), 70 g Sulfolane and 350 g PPA was heated under nitrogen to 130° C. for 24 hours. After the mixture cooled to about 80° C., it was poured into 4 l of water to precipitate the expected compound. Filtration yielded 34.3 g of the expected compound. The precipitate was purified by column chromatography on silica gel using methylene chloride as the eluent. Yield 10.5 g (30%), mp 98° C.

Anal. for $C_{13}H_7NOBr_2$:
Calculated: C, 44.29; H, 1.98; N, 3.97; Br, 45.29;
Found: C, 44.29; H, 2.01; N, 3.88; Br, 45.65.

EXAMPLE VIII

SYNTHESIS OF 2-BENZOXAZOLE-p-DICYANOBENZENE

A mixture of 2-benzoxazole-p-dibromobenzene (10.5 g, 0.027 mol), cuprous cyanide ( 5.7 g, 0.03 mol) and 150 ml of N-methyl-2-pyrrolidone was heated to reflux for 20 hours. The mixture was then poured into 100 ml of 10% NaCN solution to precipitate the product. The black solid thus obtained was chromatographed on silica gel using methylene chloride as the eluent. There was obtained 2.8 g (42%) of the expected product, m.p. 244°-7° C.

Anal. for $C_{15}H_7N_3O$:
Calculated: C, 73.46; H, 2.88; N, 17.14;
Found: C, 73.16; H, 2.90; N, 16.50.

EXAMPLE IX

SYNTHESIS OF 2-BENZOXAZOLE TEREPHTHALIC ACID

A mixture of 2-benzoxazole-p-dicyanobenzene (2.8 g, 0.011 mol) and 50 ml of 100% phosphoric acid was heated slowly to 140° C. with stirring for 24 hours. The reaction mixture was poured into water to precipitate the product. The material obtained was recrystallized from glacial acetic acid. The melting point and IR spectrum of the recrystallized material were identical to that obtained in Example II.

EXAMPLE X

POLYMERIZATION OF 2,5-DIAMINO-1,4-BENZENE DITHIOL DIHYDROCHLORIDE WITH 2-BENZOTHIAZOLE TEREPHTHALIC ACID 2,5-Diamino-1,4-benzene dithiol dihydrochloride (2.0882 g, 8.516 mmol), 2-benzothiazole terephthalic acid (2.5490 g, 8.516 mmol) and 8.78 g of polyphosphoric acid (77% $P_2O_5$) were placed in a resin flask equipped with a mechanical stirrer, nitrogen inlet/outlet tubes, a vacuum connector and a side opening on the resin flask. With nitrogen continuously flowing, the solution was evacuated to about 176 mm Hg before starting to stir and heat slowly to 90° C. for dehydrochlorination. During the dehydrochlorination, the vacuum was increased slowly to 60 mm and the temperature increased to 90° C. After 24 hours, the vacuum was resolved. The dehydrochlorination was allowed to take place at 90° C. under a nitrogen atmosphere for 20 hours. The reaction mixture was cooled to 50° C., then 6.1 g of $P_2O_5$ was added, in vacuo, thereby raising the polymer concentration to 18%. After adding the $P_2O_5$, heating was resumed. The mixture was heated at 170° C. for 20 hours, then at 190° C. for 4 hours. As the temperature was increased, opalescence began to appear at about 160° C. The mixture was then poured into water to precipitate the polymer. With the aid of a blender, the polymer was washed thoroughly with water, then dried under vacuum at 120 C for 24 hours.

[N]=19.25 dl/g. in methanesulfonic acid at 30° C.
Anal. for $C_{21}H_9N_3S_3$:
Calculated: C, 63.13; H, 2.27; N, 10.52;
Found: C, 62.21; H, 2.47; N, 16.20.

EXAMPLE XI

POLYMERIZATION OF 1,2,4,5-TETRAAMINO BENZENE TETRAHYDROCHLORIDE WITH 2-BENZOTHIAZOLE TEREPHTHALIC ACID 1,2,4,5-tetraaminobenzene tetrahydrochloride (1.7138 g, 6.033 mmol), 2-benzothiazole terephthalic acid (1.8059 g, 6.033 mmol) and 5.57 g of polyphosphoric acid (77% $P_2O_5$) were placed in a resin flask equipped with a mechanical stirrer, nitrogen inlet/outlet tubes, a vacuum connector and a side opening on the resin flask. The solution was heated at 90° C. in vacuo for 24 hours for dehydrochlorination. The reaction mixture was cooled to 60° C., then 4.04 g of $P_2O_5$ was added, in vacuo, thereby raising the polymer concentration to 18%. After adding the $P_2O_5$, heating was resumed. The reaction mixture was heated to 164° C., at which temperature the mixture became opalescent. The mixture was heated at 174° C. for 24 hours, then at 190° C. for 4 hours. Work-up, as in the preceeding Example, gave a polymer with [N]=7.5 dl/g, methanesulfonic acid at 30° C.

Anal. for $C_{21}H_{11}N_5S$:
Calculated: C, 69.10; H, 3.03; N, 19.17;
Found: C, 61.10; H, 3.41; N, 16.17.

EXAMPLE XII

POLYMERIZATION OF 4,6-DIAMINO-1,3-BENZENEDIOL DIHYDROCHLORIDE WITH 2-BENZOTHIAZOLE TEREPHTHALIC ACID 4,6-Diamino-1,3-benzenediol dihydrochloride (2.1279 g, 10.0 mmol), 2-benzothiazole terephthalic acid (2.9891 g, 10.0 mmol) and 9.96 g of polyphosphoric acid (77% $P_2O_5$) were placed in a resin flask equipped with a mechanical stirrer, nitrogen inlet/outlet tubes, a vacuum connector and a side opening on the resin flask. The solution was heated at 90° C. in vacuo for 20 hours for dehydrochlorination. The reaction mixture was cooled to 50° C., then 6.04 g of $P_2O_5$ was added, in vacuo, thereby raising the polymer concentration to 18%. After adding the $P_2O_5$, heating was resumed. The mixture was heated at 174° C. for 16 hours, then at 190° C. for 24 hours. Work-up, as in the preceeding Example, gave 3.2 g of polymer with [N]=4.1 dl/g, methanesulfonic acid at 30° C.

Anal. for $C_{21}H_9O_2N_3S$:
Calculated: C, 68.65; H, 2.47; N, 11.44; S, 8.73;
Found: C, 67.53; H, 2.63; N, 11.38; S, 8.23.

EXAMPLE XIII

POLYMERIZATION OF 2,5-DIAMINO-1,4-BENZENE DITHIOL DIHYDROCHLORIDE WITH 2-BENZOXAZOLE TEREPHTHALIC ACID 2,5-Diamino-1,4-benzene dithiol dihydrochloride (1.5544 g, 6.3 mmol), 2-benzoxazole terephthalic acid (1.7956 g, 6.3 mmol) and 10.2 g of polyphosphoric acid (83% $P_2O_5$) were placed in a resin flask equipped with a mechanical stirrer, nitrogen inlet/outlet tubes, a vacuum connector and a side opening on the resin flask. With nitrogen continuously flowing, the solution was heated slowly to 60° C. for 24 hours and 90° C. for 16 hours to remove the hydrochloride. The mixture was heated at 160° C. for 17 hours, then at 190° C. for 17 hours. Work-up, as in the preceeding Example, gave a polymer with [N]=0.96 dl/g, methanesulfonic acid at 30° C.

Anal. for $C_{21}H_9N_3O_3$:
Calculated: C, 71.79; H, 2.58; N, 11.96;
Found: C, 70.80; H, 3.61; N, 9.04.

EXAMPLE XIV

FIBER PROPERTIES

A pendant polybenzotiazole (PPBT) was prepared as described in Example X. The anisotropic reaction mixture was wet spun into fibers. The fibers were thermally treated at 550 C under a nitrogen atmosphere. The compressive strength, modulus and tensile strength of these fibers are given in Table I, below. For comparison, values for non-pendant polybenzothiazole (PBT) fibers are included.

TABLE I

| Fiber | Compressive Strength (ksi) | Modulus (msi) | Tensile Strength (ksi) |
|---|---|---|---|
| PBT | 50 | 55 | 450 |
| PPBT | 120 | 29 | 350 |

Examination of the above data reveals that although the preliminary modulus and tensile values for the PPBT are lower than for the PBT, the compressive strain properties are approximately doubled.

Various modifications of the present invention can be made in view of the foregoing disclosure without departing from the spirit and scope of the invention.

We claim:

1. A heterocyclic terephthalic acid of the formula

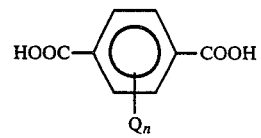

wherein n is 1 or 2 and Q is

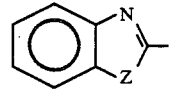

wherein Z is —O— or —S—.

2. The compound of claim 1 wherein n is 1 and Q is benzothiazole.

3. The compound of claim 1 wherein n is 1 and Q is benzoxazole.

4. The compound of claim 1 wherein n is 2 and Q is benzothiazole.

5. The compound of claim 1 wherein n is 2 and Q is benzoxazole.

* * * * *